US010070858B2

(12) United States Patent
Shelton, IV et al.

(10) Patent No.: US 10,070,858 B2
(45) Date of Patent: Sep. 11, 2018

(54) BARBED SUTURE DISPENSER

(71) Applicant: Ethicon Endo-Surgery, LLC, Guaynabo, PR (US)

(72) Inventors: Frederick E. Shelton, IV, Hillsboro, OH (US); Emily A. Schellin, Cincinnati, OH (US); Daniel J. Mumaw, Liberty Township, OH (US); Christopher J. Hess, Cincinnati, OH (US); Andrew C. Deck, Dayton, OH (US)

(73) Assignee: Ethicon LLC, Guaynabo, PR (US)

( * ) Notice: Subject to any disclaimer, the term of this patent is extended or adjusted under 35 U.S.C. 154(b) by 146 days.

(21) Appl. No.: 14/741,635

(22) Filed: Jun. 17, 2015

(65) Prior Publication Data

US 2016/0367240 A1    Dec. 22, 2016

(51) Int. Cl.
*A61B 17/04*    (2006.01)
*A61B 17/06*    (2006.01)
(Continued)

(52) U.S. Cl.
CPC ...... *A61B 17/0469* (2013.01); *A61B 17/0625* (2013.01); *A61B 17/06114* (2013.01); *A61B 17/06123* (2013.01); *A61B 17/06166* (2013.01); *A61B 50/3001* (2016.02); *A61B 17/06133* (2013.01); *A61B 2017/00473* (2013.01);
(Continued)

(58) Field of Classification Search
CPC ............ A61B 50/3001; A61B 17/0469; A61B 17/06123; A61B 17/06166; A61B 17/06114; A61B 17/0625; A61B 2017/0479; A61B 2017/00473; A61B 2017/06142; A61B 17/06133; A61B 2017/00477; A61B 2017/0608; A61B 2017/06176

See application file for complete search history.

(56) References Cited

U.S. PATENT DOCUMENTS 919,152 A * 4/1909 Gause .................... A61B 17/04
                                                       606/146
3,749,238 A * 7/1973 Taylor .............. A61B 17/06123
                                                       206/227
(Continued)

FOREIGN PATENT DOCUMENTS

WO    WO 2008/150773 A1    12/2008
WO    WO 2011/156733 A2    12/2011

OTHER PUBLICATIONS

U.S. Appl. No. 14/297,993, filed Jun. 6, 2014.
(Continued)

*Primary Examiner* — Eric Rosen
*Assistant Examiner* — Son Dang
(74) *Attorney, Agent, or Firm* — Frost Brown Todd LLC

(57) ABSTRACT

A packaging for a surgical needle comprises a cartridge. The cartridge comprises a surgical needle and a needle driver configured to engage and move the needle relative to the cartridge. The packaging further comprises a spool comprising a helical channel and a length of suture connected to the needle. At least a portion of the length of suture is wound around the spool. At least a portion of the length of suture is positioned within the helical channel. The suture may include a plurality of barbs.

13 Claims, 13 Drawing Sheets

(51) Int. Cl.
*A61B 50/30* (2016.01)
*A61B 17/062* (2006.01)
*A61B 17/00* (2006.01)

(52) U.S. Cl.
CPC ............ *A61B 2017/00477* (2013.01); *A61B 2017/0479* (2013.01); *A61B 2017/0608* (2013.01); *A61B 2017/06142* (2013.01); *A61B 2017/06176* (2013.01)

(56) References Cited

U.S. PATENT DOCUMENTS

| | | | | |
|---|---|---|---|---|
| 3,815,843 | A * | 6/1974 | Fortune | B23K 3/063 242/137.1 |
| 3,901,244 | A * | 8/1975 | Schweizer | A61B 17/04 206/63.3 |
| 4,084,692 | A * | 4/1978 | Bilweis | A61B 17/06123 206/403 |
| 4,890,615 | A * | 1/1990 | Caspari | A61B 17/0469 606/139 |
| 5,131,534 | A * | 7/1992 | Brown | A61B 17/06123 206/339 |
| 5,755,729 | A * | 5/1998 | de la Torre | A61B 17/0469 112/169 |
| 5,911,829 | A * | 6/1999 | Maksudian | A61B 17/06123 118/123 |
| 6,467,612 | B1 * | 10/2002 | Rosenfeld | A61B 17/06123 206/63.3 |
| 7,766,925 | B2 * | 8/2010 | Stokes | A61B 1/00087 606/139 |
| 8,123,764 | B2 * | 2/2012 | Meade | A61B 17/0469 606/145 |
| 8,679,136 | B2 * | 3/2014 | Mitelberg | A61B 1/00087 606/144 |
| 8,702,732 | B2 | 4/2014 | Woodard et al. | |
| 9,168,037 | B2 | 10/2015 | Woodard et al. | |
| 9,357,998 | B2 | 6/2016 | Martin et al. | |
| 9,375,212 | B2 | 6/2016 | Martin et al. | |
| 9,474,522 | B2 * | 10/2016 | Deck | A61B 17/0469 |
| 9,486,126 | B2 * | 11/2016 | West | A61B 1/018 |
| 2003/0204195 | A1 * | 10/2003 | Keane | A61B 17/0401 606/146 |
| 2005/0085851 | A1 * | 4/2005 | Fiehler | A61B 17/0057 606/213 |
| 2009/0210006 | A1 * | 8/2009 | Cohen | A61B 17/06166 606/232 |
| 2010/0016870 | A1 | 1/2010 | Campbell | |
| 2010/0230300 | A1 * | 9/2010 | Hunter | A61B 17/06114 206/63.3 |
| 2011/0046645 | A1 * | 2/2011 | McClurg | A61B 17/0469 606/145 |
| 2014/0039527 | A1 * | 2/2014 | Avelar | A61B 17/06166 606/144 |
| 2014/0166514 | A1 * | 6/2014 | Martin | A61B 17/0483 206/365 |
| 2014/0171970 | A1 | 6/2014 | Martin et al. | |
| 2015/0133967 | A1 * | 5/2015 | Martin | A61B 17/0482 606/144 |

OTHER PUBLICATIONS

U.S. Appl. No. 14/298,038, filed Jan. 30, 2015.
International Search Report and Written Opinion dated Oct. 24, 2016 for International PCT Application No. PCT/US2016/037557, 8 pages.
International Preliminary Report on Patentability dated Dec. 19, 2017 for International PCT Application No. PCT/US2016/037557, 10 pages.

* cited by examiner

BARBED SUTURE DISPENSER

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; and U.S. patent application Ser. No. 14/297,993, entitled "Jawed Cartridge receiving assembly for Needle Cartridge," filed Jun. 6, 2014, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
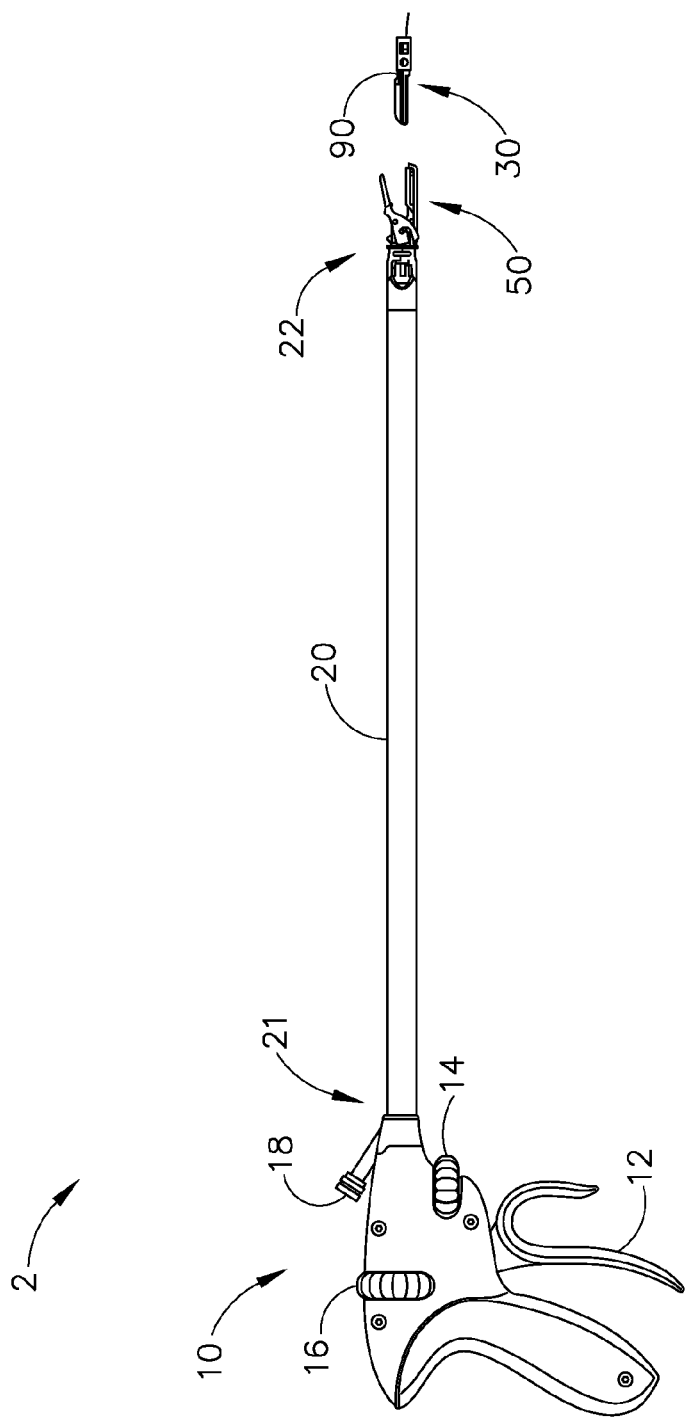
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
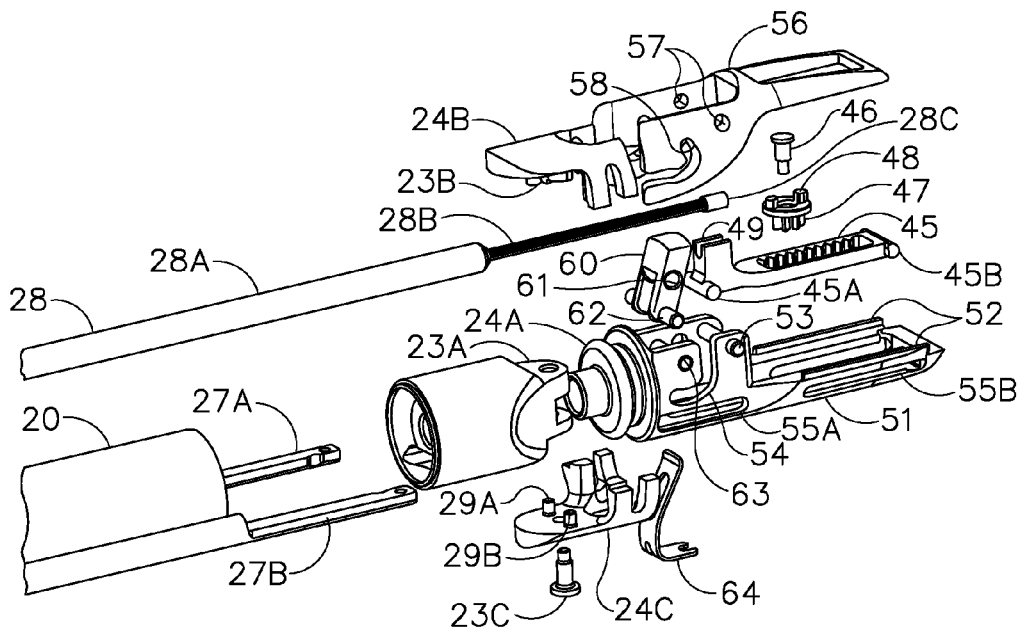
FIG. 2A depicts top perspective exploded view of a cartridge receiving assembly of the instrument of FIG. 1.
Figure 2B:
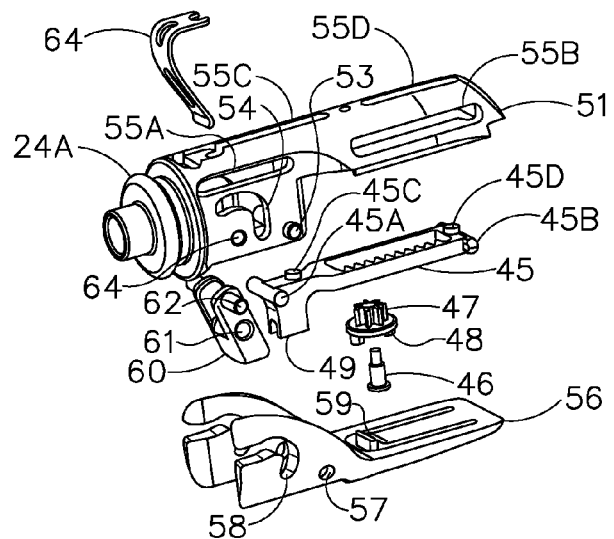
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 24C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to second input (14) to opposingly push and pull rods (27A, 27B). In other words, second input (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the open configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60)

distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
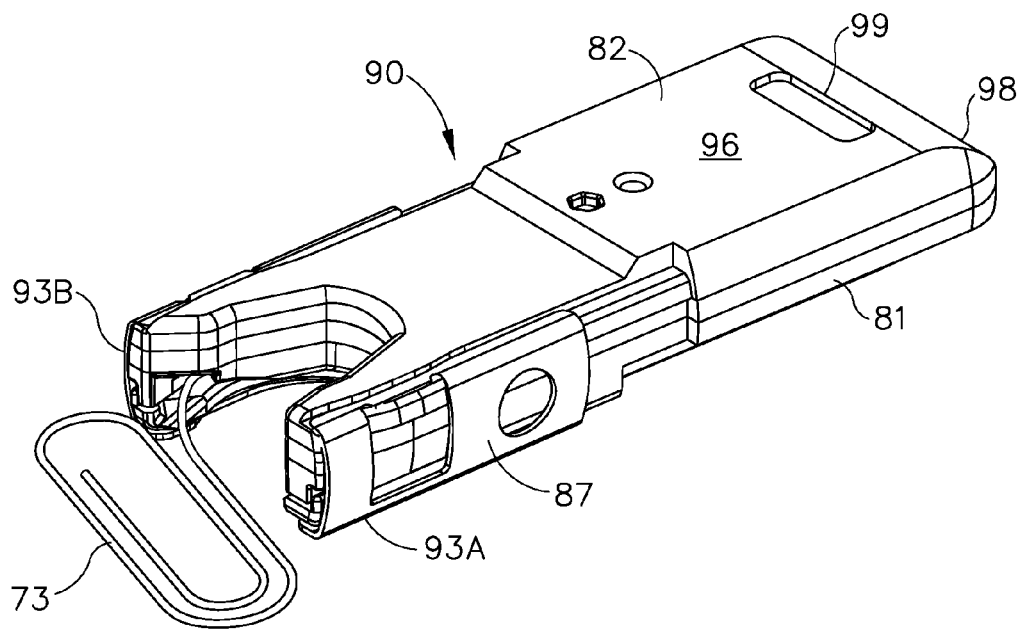
FIG. 3A depicts a top perspective view of an exemplary cartridge configured for receipt in the cartridge receiving assembly of FIG. 2A.
Figure 3B:
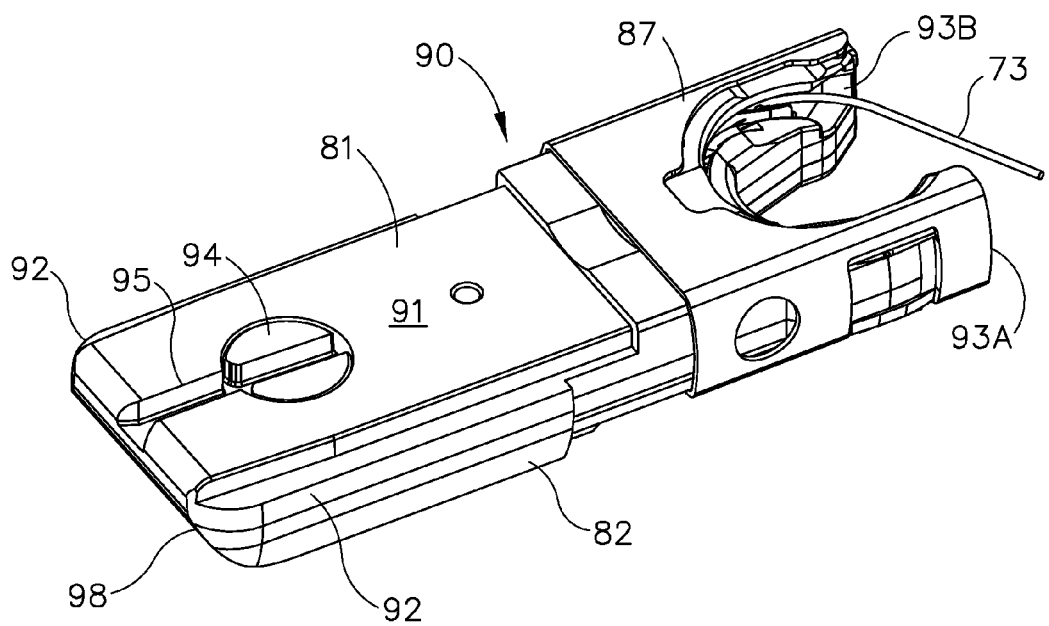
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
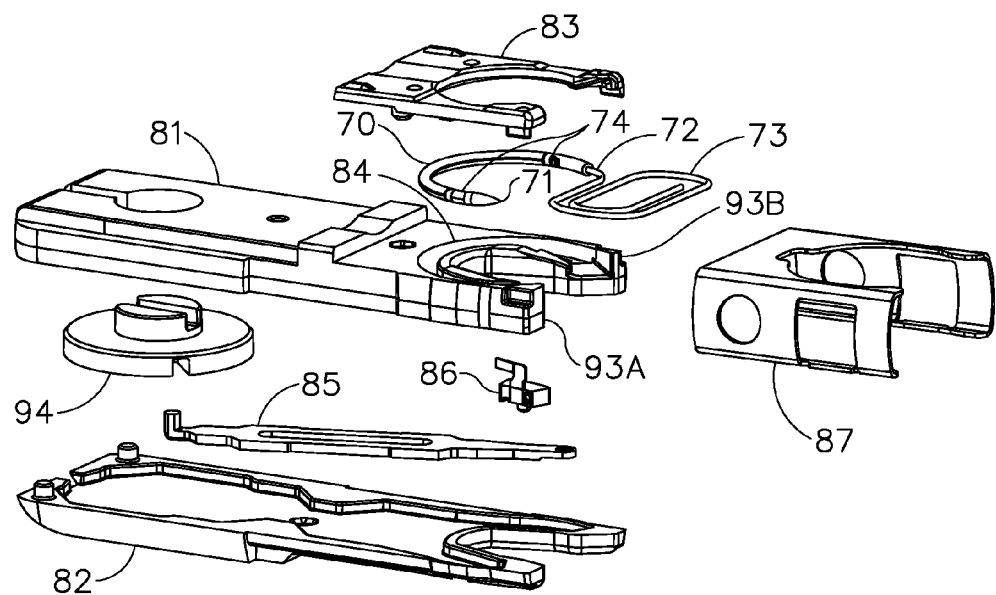
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
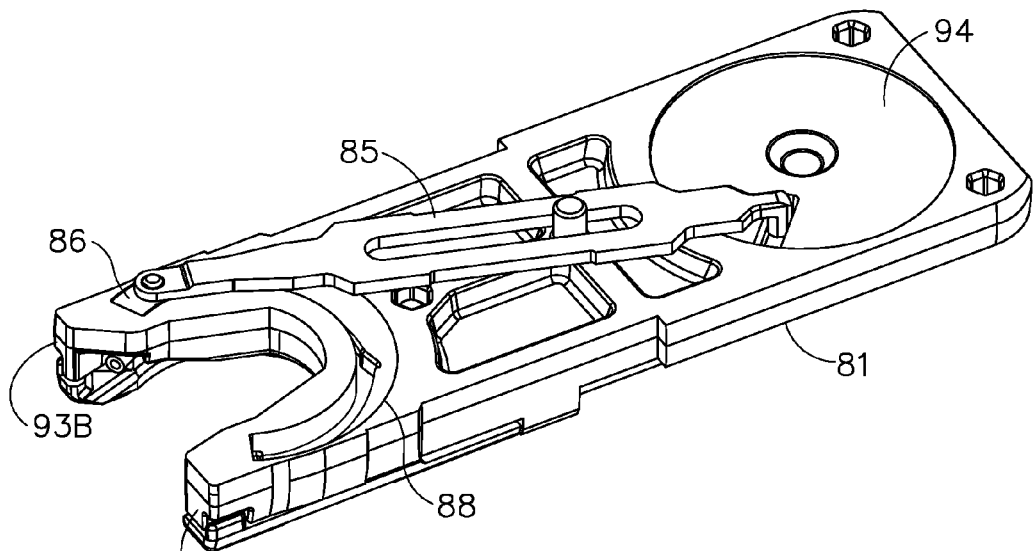
FIG. 5A depicts a perspective view of a drive assembly of the cartridge of FIG. 3A, with the drive assembly at one end of its stroke.
Figure 5B:
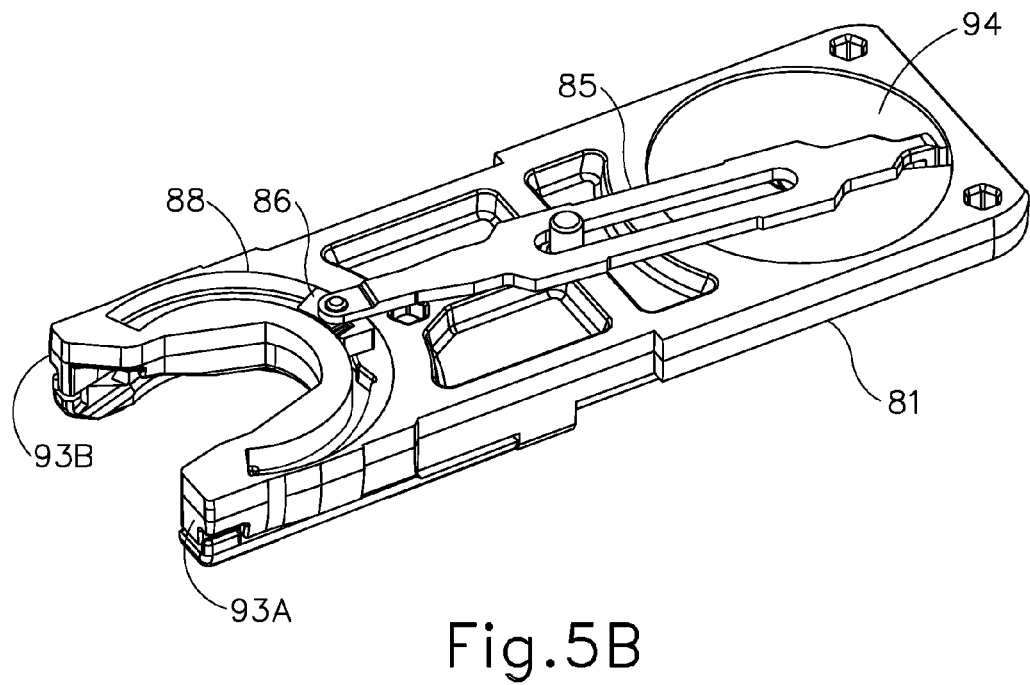
FIG. 5B depicts a perspective view of the drive assembly of FIG. 5A, with the drive assembly at mid-stroke.
Figure 5C:
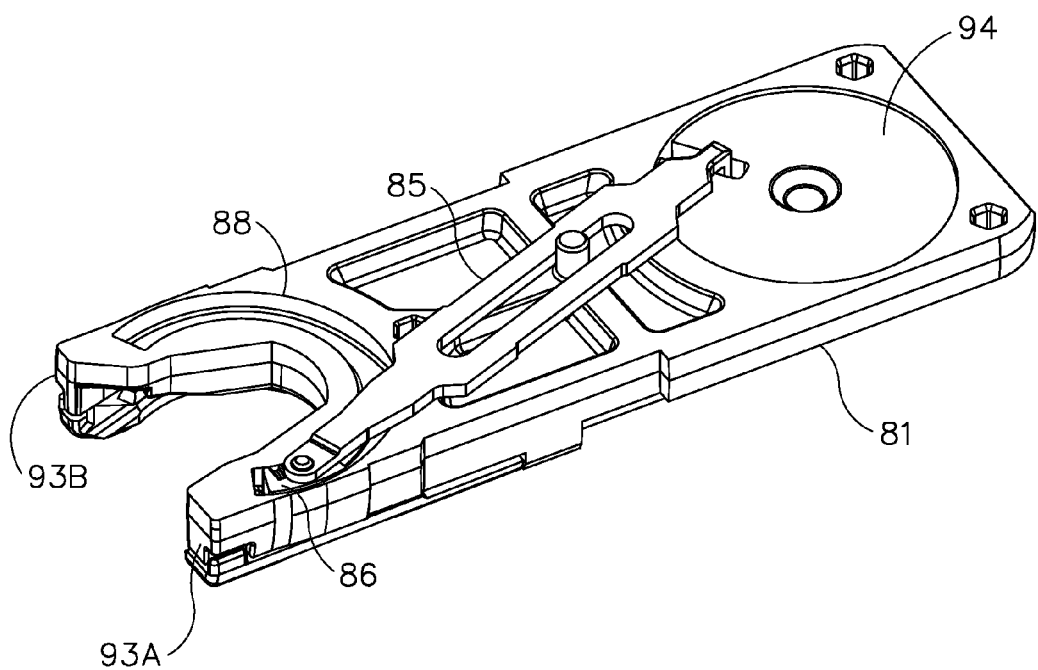
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
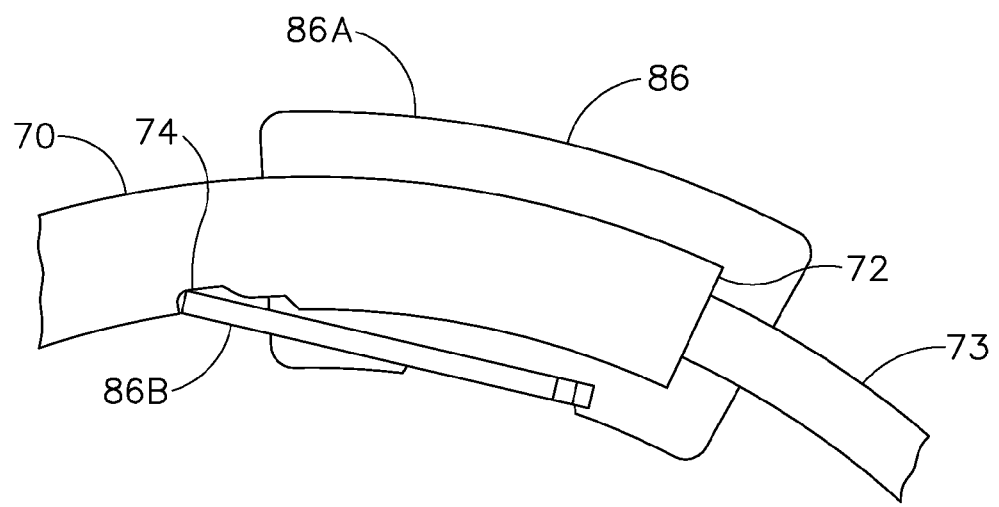
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, now U.S. Pat. No. 9,474,522, issued Oct. 25, 2016, the disclosure of which is incorporated by reference herein; and U.S. patent application Ser. No. 14/298,038, entitled "Circular Needle Applier with Cleats," filed Jan. 30, 2015, now U.S. Pat. No. 9,375,212, issued Jun. 28, 2016, the disclosure of which is incorporated by reference herein. It should be understood that such details, explanations, examples, and alternative embodiments may be readily applied to the above-described instrument (10) and subcomponents thereof.

Figure 7:
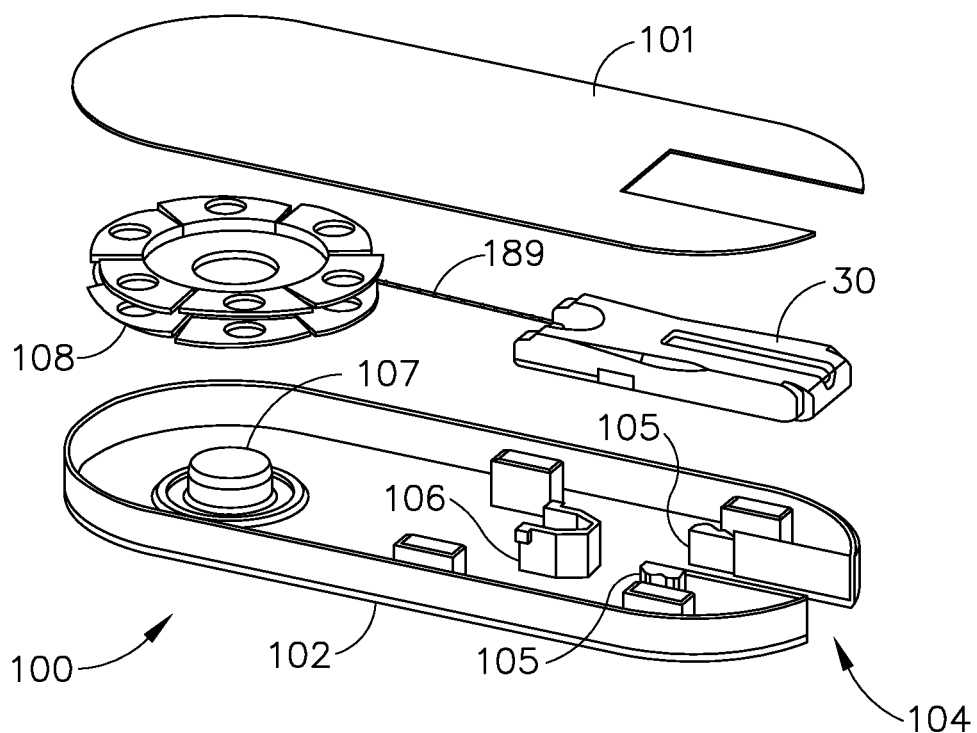
FIG. 7 depicts an exploded view of the cartridge of FIG. 3A with an exemplary suture dispenser.

FIG. 7 illustrates an embodiment of packaging (100) for a cartridge (30). The cartridge (30) may be similar to any of the prior described cartridges, and contains a surgical needle, a length of suture (73) connected to the surgical needle, a needle driver (e.g., needle driver (86) (FIGS. 5A-C)) operative to engage and move the needle relative the cartridge, and a transmission operatively connected to the needle driver. Packaging (100) has an outer shell comprising a housing (102) and a top sheet (101). The needle in cartridge (30) is in its refracted position such as in the position shown in FIG. 5A. Cartridge (30) is releasably held by arms (105). Block (106) is positioned in the U-shaped distal end on cartridge (30) and prevents the needle from exiting cartridge (30). Cartridge (30) extends into gap (104). Suture (73) extends from cartridge (30) and is coiled around bobbin (108), shown here as a dynamic spool that can rotate about the axle (107). Bobbin (108) can take alternatively take the form of a static bobbin, such as pegs or a track, around which suture (73) can be coiled.

Figure 8:
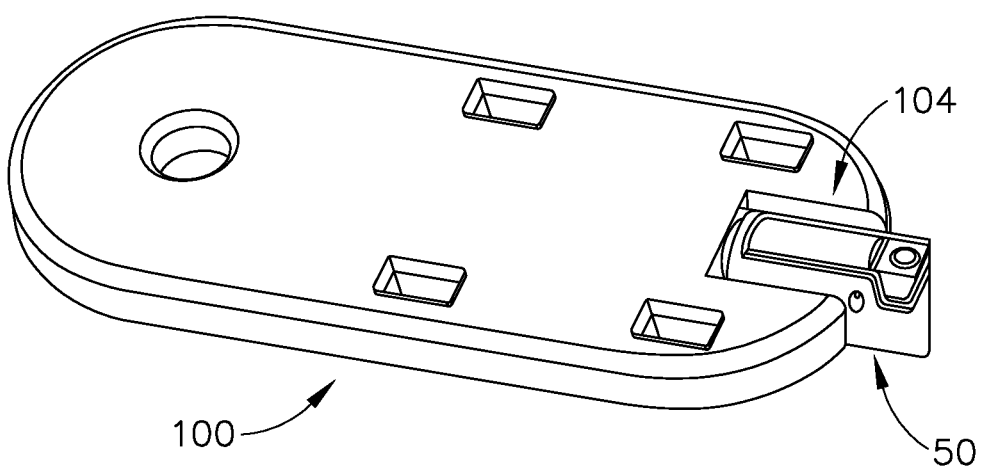
FIG. 8 depicts a perspective view of the cartridge receiving assembly of FIG. 2A engaged with the cartridge of FIG. 3A at the suture dispenser of FIG. 7.

As shown in FIG. 8, packaging (100) facilitates assembly of the cartridge (30) onto a suturing device (50). Packaging (100) provides an ergonomically friendly format to handle, align, and assembly cartridge (100) onto shaft (20) of suturing device (50), while keeping the needle safely isolated from the user. Once assembled and attached, withdrawing shaft (20) will pull cartridge (30) from packaging (100) and suture (73) will reel out from bobbin (108) and be ready for use.

II. Exemplary Suture Dispenser

In some situations, an operator may wish to use a barbed suture, such as the STRATAFIX™ suture by Ethicon, Inc. (Somerville, N.J.), when operating instrument (2) during a suturing procedure. Due to the nature of the barbs of the barbed suture, an operator must be careful to prevent the barbs of the barbed suture from overlapping one another before or during use, to prevent, for example, tangling of and snagging of the suture on itself. Even when exercising the utmost care, tangling and snagging may occur, since some existing packaging such as packaging (100) may not properly accommodate barbed sutures. Therefore, the storage of barbed sutures in packaging (100) may lead to the above mentioned issues and may prevent an operator from effectively using the barbed sutures.

A. Exemplary Suture Dispenser with End Cartridge Loading

Figure 9:
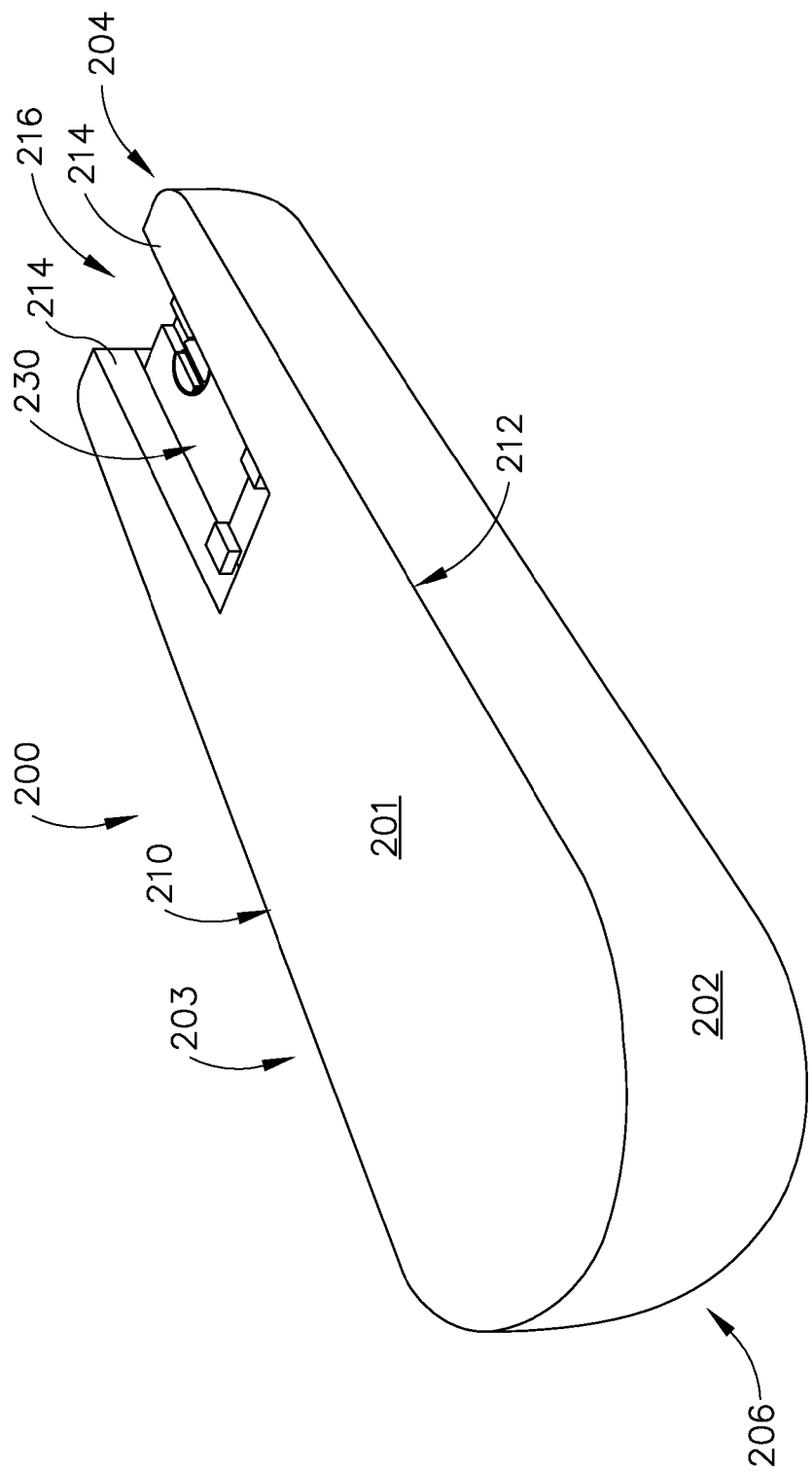
FIG. 9 depicts a perspective view of the cartridge of FIG. 3A with an exemplary alternative suture dispenser.
Figure 10:
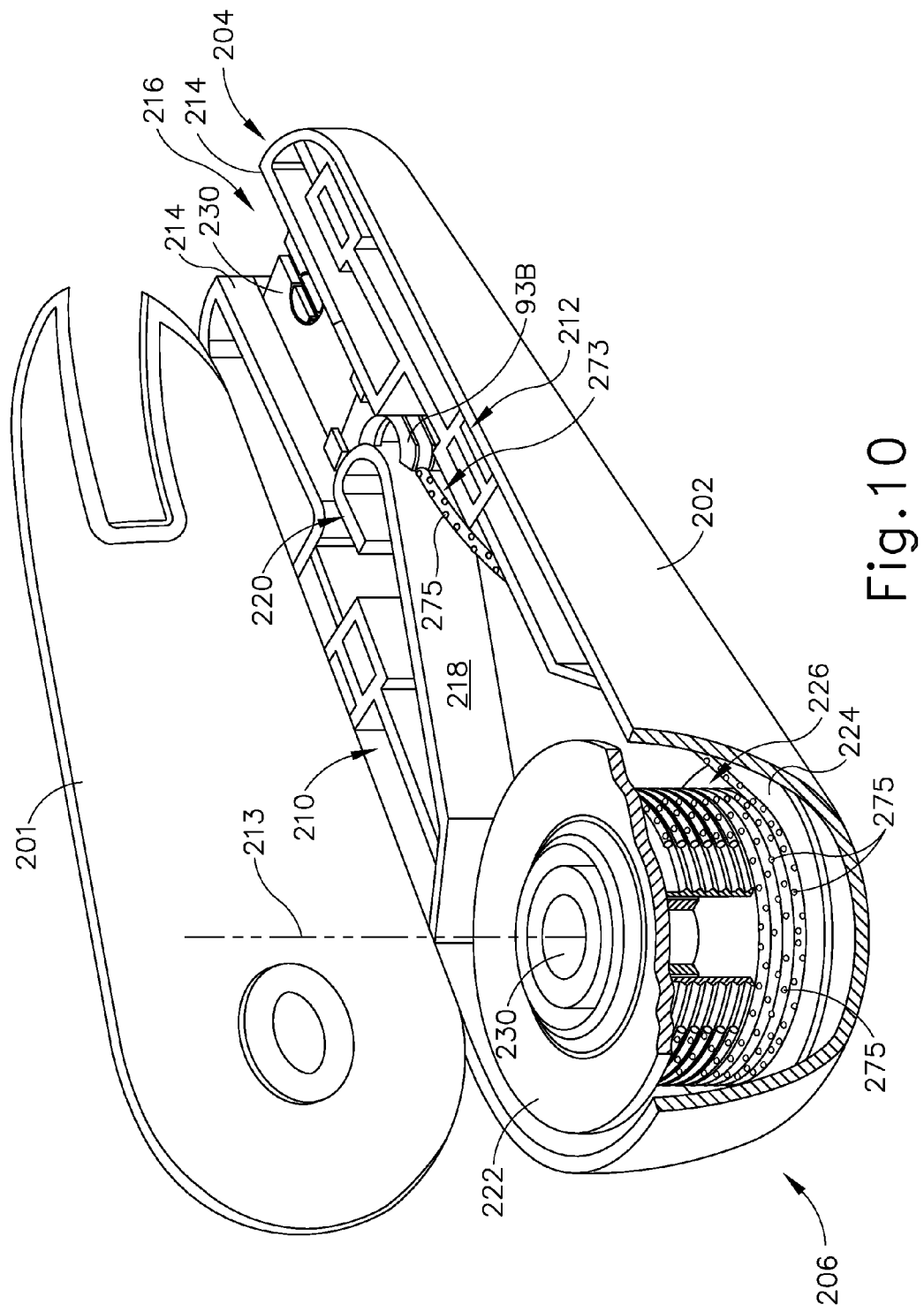
FIG. 10 depicts a perspective view of the cartridge of FIG. 3A in the suture dispenser of FIG. 9, with a portion of the suture dispenser opened to reveal internal components.
Figure 11:
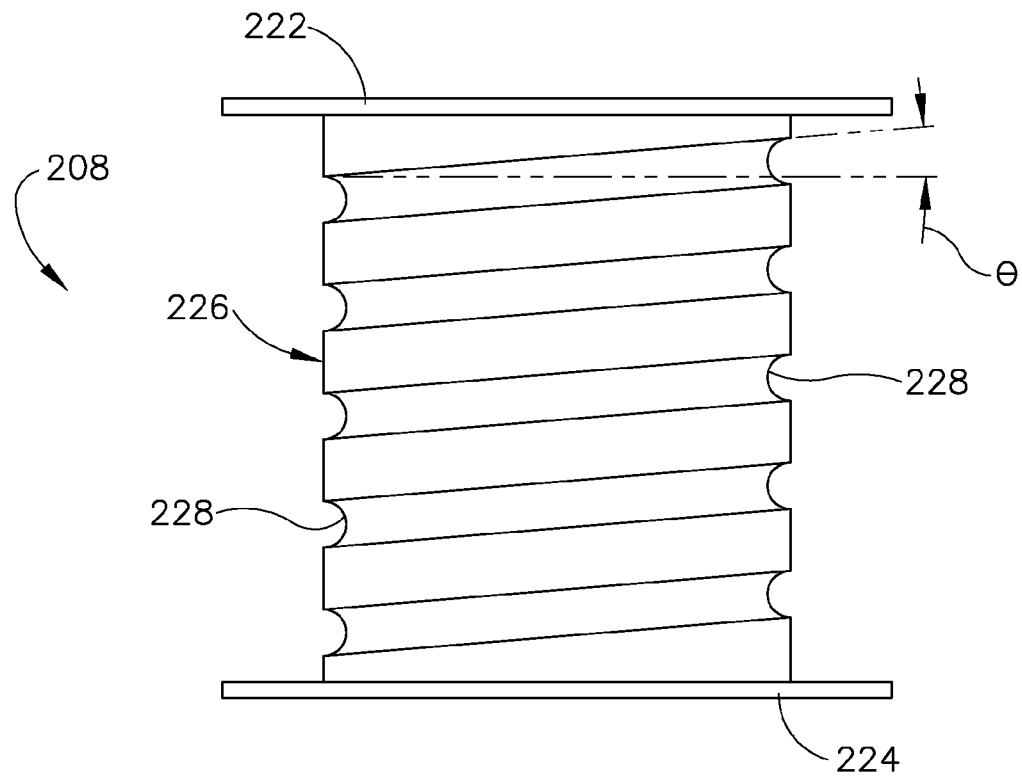
FIG. 11 depicts a side elevational view of a suture spool of the suture dispenser of FIG. 10.

FIGS. 9-11 illustrate an example of suture dispenser packaging (200) for a cartridge (230). Cartridge (230) is configured and operable substantially similar to cartridge (30), and contains a surgical needle (e.g., needle (70)) a length of suture (273) connected to the surgical needle, a needle driver (e.g., needle driver (86) (FIGS. 5A-5C)) that is operative to engage and move the needle relative the cartridge (230), and a drive assembly that is operatively connected to the needle driver. Cartridge (230) may thus be readily received in cartridge receiving assembly (50) and may thereby be actuated by instrument (2). The needle is initially provided in cartridge (230) in a retracted position (e.g., the position shown in FIG. 5A). In the example shown, the length of suture (273) comprises barbed suture, with a plurality of barbs (275). Suture (273) is contained on a spool (208), as discussed in further detail below. However, it will be understood that packaging (200) is configured for use with all types of sutures, including barbed and non-barbed sutures.

Packaging (200) includes a housing (203) comprising a top sheet or lid (201) and a shell (202). Housing (203) has a proximal end (204) and a distal end (206). In the present example, shell (203) includes a greater depth at distal end (206) to accommodate spool (208). Housing (203) further includes a first side (210) and a second side (212). Proximal end (204) includes a pair of opposing arms (214) defining a gap or recess (216) therebetween. As shown in the present example, cartridge (230) is received in gap (216) such that cartridge (230) is frictionally held by arms (214). In addition or in the alternative, packaging (200) may include one or more latches, clips, clamping features, and/or any other suitable kinds of features that may releasably retain cartridge (230) relative to housing (203). Packaging (200) further includes a flange (218) extending at an oblique angle relative to a central longitudinal axis of shell (202). Flange includes a hook-shaped portion (220) positioned in shell (202). Hook-shaped portion (220) is sized and configured to be at least partially received between arms (93A, 93B) of cartridge (230) such that the frictional engagement between arms (93A, 93B) and hook-shaped portion (220) also maintains cartridge (230) relative to packaging (200).

Referring to FIGS. 10-11, spool (208) includes a first flange (222), a second flange (224), and a generally cylindraceous body (226) therebetween. As shown in the present example, spool (208) includes a helical channel (228) which receives suture (273). Therefore, barbs (290) of suture (273) will be less likely to interfere with one another while suture (273) is stored in packaging (200) and while suture (273) is withdrawn from packaging (200). This is because in the present example, no portions of suture (273) overlap one another during storage, thus preventing barbs (276) of barbed suture (273) from catching on one another. As shown spool (208) includes a central channel (230) that receives a rod (not shown) extending from shell (202) that is fixed to shell (202). Spool (208) extends along an axis (213). In the example shown, spool (208) is configured to rotate about the rod and axis (213). However, in some examples, spool (208) may be fixedly connected to a rod or other structure that is configured to rotate relative to housing (203). In the present example, a leading end of suture (273) is connected to needle and trailing end of suture (273) is disposed on spool (289).

Once cartridge (230) is secured in cartridge receiving assembly (50) of instrument (2) in the manner described above, withdrawing shaft (20) will pull cartridge (230) from packaging (200), and suture (273) will reel out from spool (208). Particularly, the frictional engagement between suture (273) and helical channel (228) will cause a rotation of spool (208) upon the sufficient pulling force of suture (273). Helical channel (228) includes a pitch angle (θ) (FIG. 11) that will not hamper the rotation of spool (208) in response to spool (208) being subjected to the tangential rotational force from the frictional engagement between spool (208) (i.e., helical channel (228)) and suture (273). In the present example, trailing end of suture (273) is removably coupled to spool (208) in a manner that allows the suture (273) to remain coupled to spool (280) absent a sufficient pulling force from an operator. However, upon the application of a sufficient force, trailing end of suture (273) may be removed from spool (289) after the remainder of suture (273) has reeled off of spool (208), and thus suture (273) will be ready for use in a suturing operation. Suturing instrument (2) with cartridge (230) loaded in cartridge receiving assembly (50) will operate in the same manner as suturing instrument (2) with cartridge (30) loaded in cartridge receiving assembly (50) as described above.

B. Exemplary Suture Dispenser with Central Cartridge Loading

Figure 12:
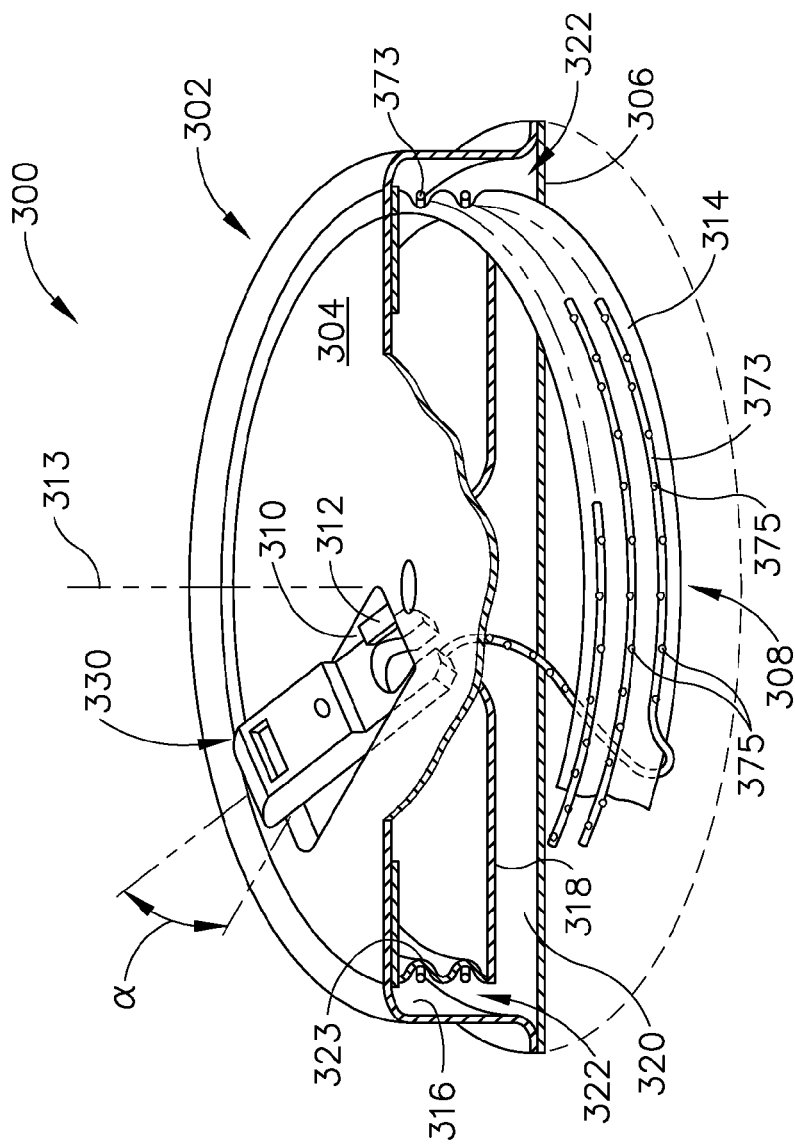
FIG. 12 depicts a perspective view of the cartridge of FIG. 3A with another exemplary alternative suture dispenser, with a portion of the suture dispenser omitted to reveal internal components.
Figure 13A:
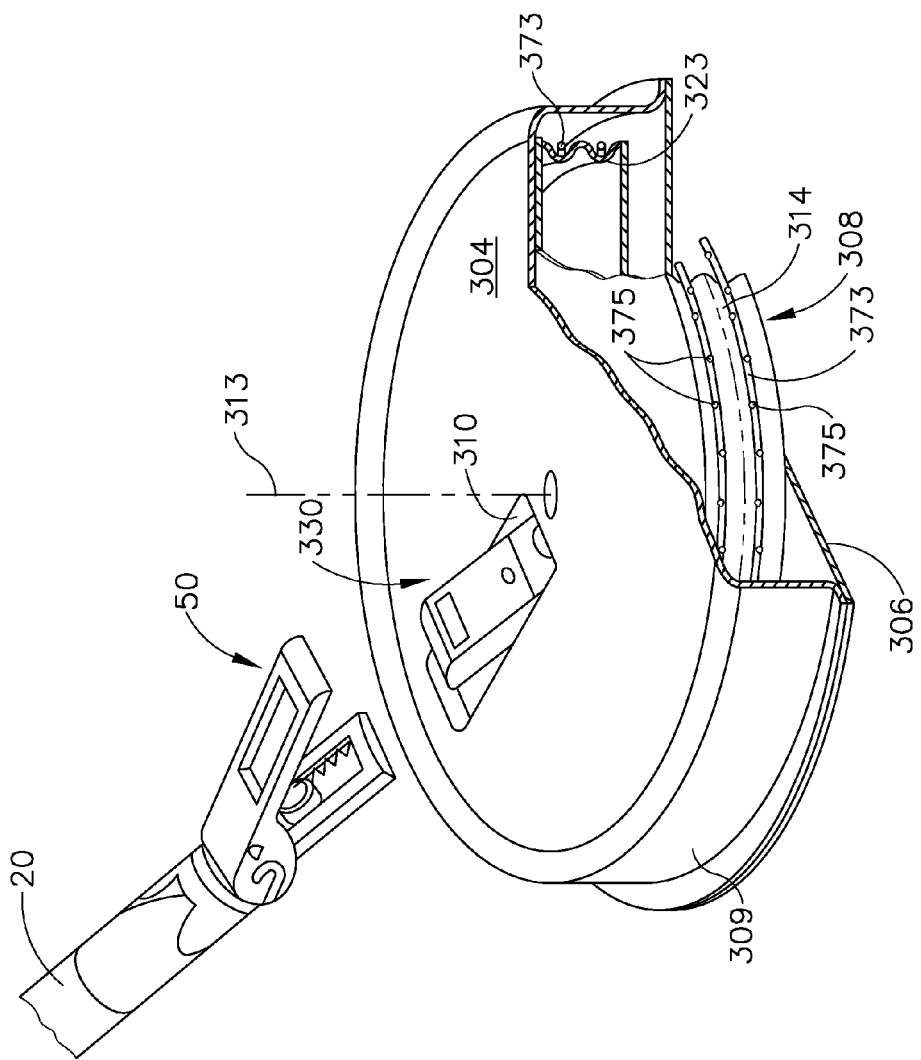
FIG. 13A depicts a perspective view of the cartridge receiving assembly of FIG. 2A approaching the suture dispenser of FIG. 12.
Figure 13B:
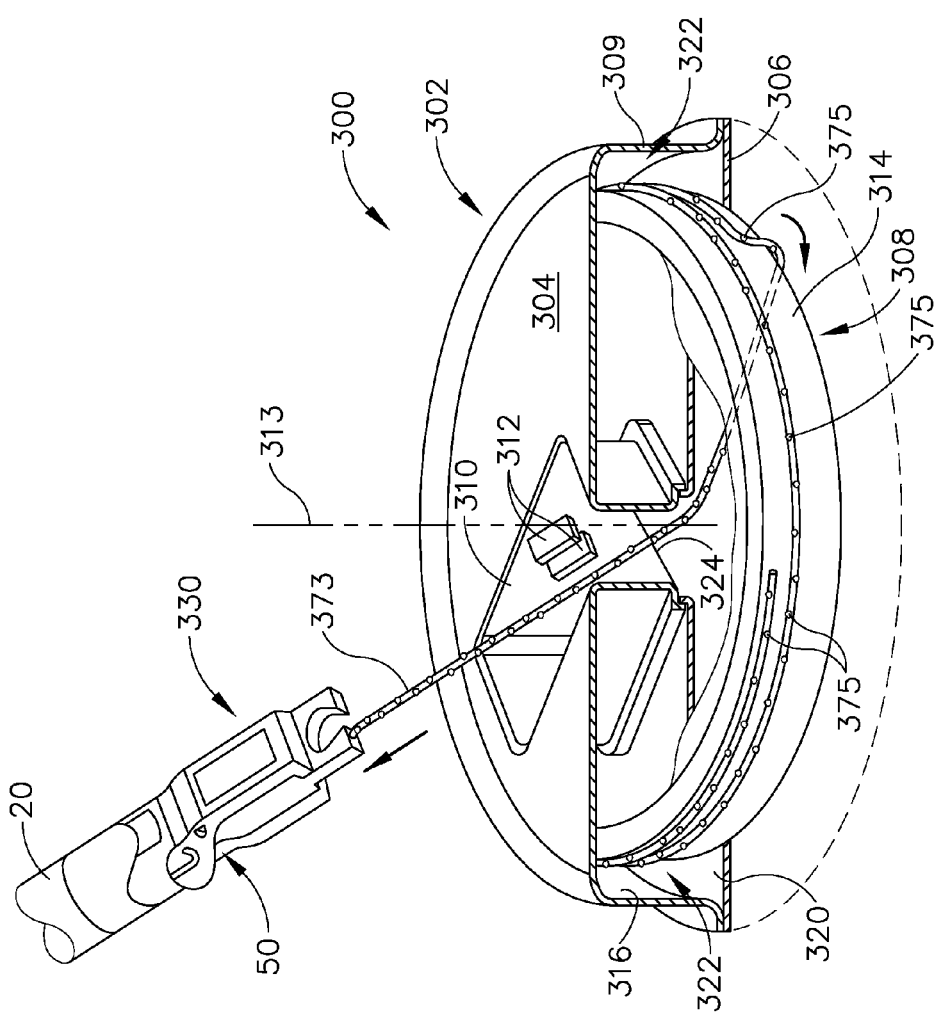
FIG. 13B depicts a perspective view of the cartridge receiving assembly of FIG. 2A engaged with the cartridge of FIG. 3A, pulling suture from the suture dispenser of FIG. 12.

FIGS. 12-13B illustrate another example of suture dispenser packaging (300) for another cartridge (330). Cartridge (330) is configured and operable substantially similar to cartridges (30, 230), and contains a surgical needle (e.g., needle (70)), a length of suture (373) connected to the surgical needle, a needle driver (e.g., needle driver (86) (FIGS. 5A-5C)) that is operative to engage and move the needle relative the cartridge (330), and a drive assembly that is operatively connected to the needle driver. Cartridge (330) may thus be readily received in cartridge receiving assembly (50) and may thereby be actuated by instrument (2). The needle initially provided in cartridge (330) in a retracted position, such as in the position shown in FIG. 5A. In the example shown, the length of suture (373) comprises a barbed suture, with a plurality of barbs (375). Suture (373) is contained on a spool (308), as discussed in further detail below. However, it will be understood that packaging (300) is configured for use with all types of sutures, including barbed and non-barbed sutures.

Packaging (300) includes a housing (302) having a first side (304) and a second side (306). Housing (302) generally defines a disk shape with the first side (304) defining a top portion, the second side (306) defining a bottom portion, and a sidewall (309) extending between the top and bottom portions, and defining a curved surface. First side (304) includes a recess (310) extending from the first side (304) toward the second side (306). Recess (310) has a shape that complements the shape of cartridge (330) which, as shown in FIG. 12, is partially received within recess (310). Recess (312) includes a ramp that is oriented at an oblique angle (α) (FIG. 12) relative to first side (304), and at an angle (90°−α) relative to axis (313) (FIG. 13A). In the example shown, α is an acute angle. Housing (302) includes fingers (312) in recess (310) that are configured to frictionally engage one or both of arms (93A, 93B) of cartridge (330). In addition or in the alternative, packaging (300) may include one or more latches, clips, clamping features, and/or any other suitable kinds of features that may releasably retain cartridge (330) relative to housing (302).

In the present example, packaging (300) further includes a spool (308) that is enveloped by sidewall (309) and second side (306). Spool (308) of the present example is fixed relative to housing (302), such that spool (308) does not rotate relative to housing (302). In some other versions, however, spool (308) is rotatable within housing (302). As shown, an outer portion (314) of spool (308) is positioned radially inwardly of inner portion (316) of flange. Similarly, a lower portion (318) of spool (308) is positioned axially above inner portion (320) of second side (306). Therefore, in the present example, there is a space (322) defined between spool (308) and housing (302). Spool (308) includes a helical channel (323) which, as shown in the present example, receives and stores a portion of length of suture (373). Recess (310) includes an aperture (324) that provides a pathway for communication of suture (373) from space (322) to recess (310). Thus, as best seen in FIGS. 12 and 13B, the length of suture (373) extending from cartridge (330) extends through aperture (324), into space (322) along lower portion (320) of spool (308), and is wrapped around spool (308) within helical channel (323). As shown, due to the configuration of helical channel (323), no portions of suture (373) overlap one another during storage, thus preventing barbs (375) of barbed suture from catching on one another.

Referring to FIGS. 13A-13B, once cartridge (330) is secured in cartridge receiving assembly (50) of instrument (2) in the manner described above, withdrawing shaft (20) will pull cartridge (330) from packaging (300) and suture (373) will unravel under and around spool (308). In some examples, an operator may also hold packaging (300) in a stationary position (e.g., with a hand, instrument, etc.) so that packaging (300) does not move relative to instrument (10). In some examples, a trailing end of suture (373) may be removably coupled to housing (302) or spool (308) such that absent a sufficient force, trailing end of suture (373) remains coupled to housing or spool (308). However, in response to a sufficient force, such as after most of suture (373) has unraveled from spool (308) in response to pulling on cartridge (330) with suturing device (50), the trailing end of suture (373) is configured to decouple from housing (302) or spool (308). Moreover, in some examples, at least a portion of helical channel (323) may be configured to frictionally hold at least some portions of suture (373) relative to spool (308). As another merely illustrative alternative, suture (373) may be loosely received in helical channel (323). Once suture (373) is unraveled from spool (308) and removed from packaging (300), suture (273) will be ready for use in a suturing operation. Suturing instrument (2) with cartridge (330) loaded in cartridge receiving assembly (50) will operate in the same manner as suturing instrument (2) with cartridge (30) loaded in cartridge receiving assembly (50) as described above III. Exemplary Combinations The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A packaging for a surgical needle, comprising: (a) a cartridge comprising: (i) a surgical needle, and (ii) a needle driver configured to engage and move the needle relative to the cartridge; (b) a spool comprising a helical channel; and (c) a length of suture connected to the needle, wherein at least a portion of the length of suture is wound around the spool, wherein at least a portion of the length of suture is positioned within the helical channel.

EXAMPLE 2

The packaging of Example 1, wherein the suture comprises a plurality of barbs.

EXAMPLE 3

The packaging of any one or more of Examples 1 through 2, further comprising a housing surrounding at least a portion of the spool.

EXAMPLE 4

The packaging of Example 3, wherein the spool is fixed relative to the housing.

EXAMPLE 5

The packaging of any one or more of Examples 3 through 4, wherein the spool is configured to rotate relative to the housing.

EXAMPLE 6

The packaging of any one or more of Examples 1 through 5, wherein the spool extends along an axis, wherein the cartridge is coupled to the body such that the cartridge extends perpendicularly relative to the axis.

EXAMPLE 7

The packaging of any one or more of Examples 1 through 5, wherein the spool extends along an axis, wherein the cartridge is coupled to the body such that the cartridge extends at an oblique angle relative to the axis.

EXAMPLE 8

The packaging of any one or more of Examples 1 through 7, further comprising a housing, wherein the housing comprises: (i) a top portion, (ii) a bottom portion, and (ii) a sidewall extending between the top and bottom portions.

EXAMPLE 9

The packaging of Example 8, wherein the housing is generally disk shaped.

EXAMPLE 10

The packaging of any one or more of Examples 8 through 9, wherein the housing surrounds the spool, wherein the packaging further comprising a space between the spool and an inner portion of the sidewall and between an inner portion of the bottom portion.

EXAMPLE 11

The packaging of Example 10, wherein the housing comprises an aperture in communication with the space, wherein a portion of the length of suture extends through the aperture and into the space.

EXAMPLE 12

The packaging of Example 11, wherein at least a portion of the length of suture extends along a lower portion of the spool.

EXAMPLE 13

The packaging of any one or more of Examples 8 through 12, wherein the top and bottom portions are parallel to one another.

EXAMPLE 14

The packaging of any one or more of Examples 8 through 13, wherein the top portion includes a recess, wherein at least a portion of the cartridge is received within the recess.

EXAMPLE 15

The packaging of Example 13, wherein the housing comprises engagement features in the recess, wherein the engagement features are configured to engage a portion of the cartridge to removably couple the cartridge to the housing.

EXAMPLE 16

A packaging for a surgical needle, comprising: (a) a housing, wherein the housing comprises an upper portion and a lower portion; (b) a cartridge comprising: (i) a surgical needle, and (ii) a needle driver operative to engage and move the needle relative to the cartridge, wherein the cartridge is coupled to the housing, wherein the cartridge is disposed at an oblique angle relative to at least one of the upper portion or lower portion; (c) a spool, wherein at least a portion of the spool is disposed in the housing; and (d) a length of suture connected to the needle, wherein at least a portion of the length of suture is wound around the spool.

EXAMPLE 17

The packaging of Example 17, wherein the housing comprises a proximal end and a distal end, wherein the housing includes a greater depth at the distal end, wherein the spool is disposed at the distal end.

EXAMPLE 18

The packaging of any one or more of Examples 16 through 17, wherein the length of suture is wound helically around the spool.

EXAMPLE 19

The packaging of any one or more of Examples 16 through 18, wherein a trailing end of the suture is removably coupled to the spool.

EXAMPLE 20

A method for preparing an instrument for use, comprising: (a) providing an instrument, the instrument comprising an elongate shaft wherein the elongate shaft comprises a distal end; (b) providing a packaging, the packaging comprising: (i) a cartridge, comprising: (A) a surgical needle, and (B) a needle driver operative to engage and move the needle relative the cartridge, (ii) a spool comprising a helical channel, and (iii) a length of suture connected to the needle, wherein at least a portion of the length of suture is wound around the spool, wherein at least a portion of the length of suture is positioned within the helical channel; and (c) coupling the distal end of the shaft to the cartridge; and (d) directing the cartridge and the shaft away from the packaging, thereby unwinding the suture from the spool.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A packaging for a surgical needle, comprising:
   (a) a package housing;
   (b) a cartridge releasably retained in the package housing, wherein the cartridge comprises:
      (i) a surgical needle,
      (ii) a needle driver configured to engage and move the needle relative to the cartridge; and
      (iii) a pair of arms;
   (c) a spool comprising a helical channel;
   (d) a flange configured to frictionally engage the cartridge between the pair of arms to thereby releasably secure the cartridge to the package housing; and
   (e) a length of suture connected to the needle, wherein at least a portion of the length of suture is wound around the spool, wherein at least a portion of the length of suture is positioned within the helical channel.

2. The packaging according to claim 1, wherein the suture comprises a plurality of barbs.

3. The packaging according to claim 1, wherein the package housing surrounds at least a portion of the spool.

4. The packaging according to claim 3, wherein the spool is fixed relative to the package housing.

5. The packaging according to claim 3, wherein the spool is configured to rotate relative to the package housing.

6. The packaging according to claim 1, wherein the spool extends along an axis, wherein the cartridge is coupled to the package housing such that the cartridge extends perpendicularly relative to the axis.

7. The packaging according to claim 1, wherein the package housing comprises:
   (i) a top portion,
   (ii) a bottom portion, and (ii) a sidewall extending between the top and bottom portions.

8. The packaging according to claim 7, wherein the top portion includes a recess, wherein at least a portion of the cartridge is received within the recess.

9. The packaging according to claim 8, wherein the package housing comprises engagement features in the recess, wherein the engagement features are configured to engage a portion of the cartridge to removably couple the cartridge to the package housing.

10. A packaging for a surgical needle, comprising:
(a) a housing, wherein the housing comprises an upper portion and a lower portion, wherein the lower portion includes a securement feature;
(b) a cartridge, wherein at least a portion of the cartridge is slidably received in the housing, the cartridge comprising:
(i) a surgical needle, and
(ii) a pair of arms, wherein the arms are disposed in the housing, wherein the securement feature is sized and shaped to fit between the arms when the cartridge is slidably received in the housing such that the securement feature is configured to frictionally retain the cartridge within the housing; and
(iii) a needle driver operative to engage and move the needle relative to the cartridge, wherein the cartridge is removably coupled to the housing;
(c) a spool, wherein at least a portion of the spool is disposed in the housing;
(d) a length of suture connected to the surgical needle, wherein at least a portion of the length of suture is wound around the spool.

11. The packaging according to claim 10, wherein the housing comprises a proximal end and a distal end, wherein the housing includes a greater depth at the distal end, wherein the spool is disposed at the distal end.

12. The packaging according to claim 10, wherein the length of suture is wound helically around the spool.

13. The packaging according to claim 10, wherein a trailing end of the suture is removably coupled to the spool.

* * * * *